United States Patent
Klistorner et al.

(10) Patent No.: US 8,075,137 B2
(45) Date of Patent: Dec. 13, 2011

(54) STIMULUS METHOD FOR MULTIFOCAL VISUAL EVOKED POTENTIAL

(75) Inventors: Alexander Klistorner, Mt Colah (AU); Stuart Lindsay Graham, Pymble (AU)

(73) Assignee: Objectivision Limited (AU)

( * ) Notice: Subject to any disclaimer, the term of this patent is extended or adjusted under 35 U.S.C. 154(b) by 0 days.

(21) Appl. No.: 12/527,466

(22) PCT Filed: Feb. 15, 2008

(86) PCT No.: PCT/AU2008/000205
§ 371 (c)(1),
(2), (4) Date: Dec. 29, 2009

(87) PCT Pub. No.: WO2008/098310
PCT Pub. Date: Aug. 21, 2008

(65) Prior Publication Data
US 2010/0091245 A1    Apr. 15, 2010

(30) Foreign Application Priority Data
Feb. 16, 2007    (AU) ................................ 2007900803

(51) Int. Cl.
*A61B 3/00* (2006.01)
*A61B 3/10* (2006.01)
(52) U.S. Cl. ....................................... 351/246; 351/205
(58) Field of Classification Search ........... 351/200–246
See application file for complete search history.

(56) References Cited

U.S. PATENT DOCUMENTS

| | | | |
|---|---|---|---|
| 4,493,539 A * | 1/1985 | Cannon, Jr. ................... | 351/205 |
| 4,649,482 A * | 3/1987 | Raviv et al. ................... | 600/544 |
| 4,736,751 A * | 4/1988 | Gevins et al. ................. | 600/545 |
| 4,846,567 A | 7/1989 | Sutter .......................... | 351/224 |
| 6,477,407 B1 * | 11/2002 | Klistorner et al. ............ | 600/544 |

FOREIGN PATENT DOCUMENTS

| | | |
|---|---|---|
| DE | 19621960 A1 | 4/1997 |
| DE | 19961323 A1 | 6/2001 |
| WO | 9934727 A1 | 7/1999 |

(Continued)

OTHER PUBLICATIONS

Klistorner et al. "Multifocal Topographic Visual Evoked Potential: Improving Objective Detection of Local Visual Field Defects", Investigative Ophthalmology & Visual Science May 1998, vol. 39, No. 6m p. 937-950.

(Continued)

*Primary Examiner* — Mohammed Hasan
(74) *Attorney, Agent, or Firm* — Brooks Kushman P.C.

(57) ABSTRACT

Disclosed herein is a method of producing a stimulus for electrophysiological assessment of a visual field. The method comprises the steps of: generating a pseudorandom sequence of elements selected from at least two different element types, wherein elements of the sequence are assigned equal time intervals; and displaying the pseudorandom sequence. Each element of a first element type is associated with a baseline value, the baseline value being constant throughout a respective assigned time interval. Each time interval assigned to an element of a second element type is divided into a plurality of portions, each successive portion being associated with a display value of the element, wherein display values associated with, adjacent portions differ from one another, and further wherein display values associated with at least two of the portions are different from the baseline value.

21 Claims, 10 Drawing Sheets

FOREIGN PATENT DOCUMENTS

| | | | |
|---|---|---|---|
| WO | 9958046 | A1 | 11/1999 |
| WO | 0139659 | A1 | 6/2001 |
| WO | 0178586 | A1 | 10/2001 |

OTHER PUBLICATIONS

James, "The Pattern-Pulse Multifocal Visual Evoked Potential" Investigative Ophthalmology & Visual Science Feb. 2003, vol. 44, No. 2, p. 879-890.

Graham et al. "Clinical Application of Objective Perimetry Using Multifocal Visual Evoked Potentials in Glaucome Practice", Arch Ophthalmol. Jun. 2005, vol. 123, p. 729-739.

Baseler et al. "The topography of Visual Evoked Response Properties Across the visual Field", Electroencephalography and Clinical Neurophysiology 1994, vol. 90, p. 65-81, July.

Fraser et al. "Multifocal Visual Evoked Potential Analysis of Inflammatory or Demyelinating Optic Neuritis" Ophthalmology Feb. 2006, vol. 113, No. 2, p. 315-323E2, June.

Goldberg et al. "Multifocal Objective Perimetry in the Detection of Glaucomatous Field Loss", American Journal of Ophthalmology Jan. 2002, vol. 133, No. 1, p. 29-39.

Hood et al. "Multifocal VEP and Ganglion Cell Damage: Applications and Limitations for the Study of Glaucoma", Progress in Retinal and Eye Research 2003, vol. 22, p. 201-251.

Jeffreys et al. "Source Locations of Pattern-Specific Components of Human Visual Evoked Potentials. II. Component of Extrastriate Cortical Origin", Exp. Brain Res. 1972, vol. 16, p. 22-40.

Klistorner et al. "Objective Perimetry in Glaucoma", Ophthalmology Dec. 2000, vol. 107, No. 12, 2283-2299.

Zhang, "Simultaneously Recording Local Luminance Responses, Spatial and Temporal Interactions in the Visual System with m-Sequences", Vision Research 2003, vol. 43, p. 1689-1698, December.

Srebro, "The Topography of Scalp Potentials Evoked by Pattern Pulse Stimuli", Vision Res. 1987, vol. 27, No. 6, p. 901-914, December.

Srebro, "Localization of Visually Evoked Cortical Activity in Humans", J. Physiology 1985, vol. 360, p. 233-246, January.

Link et al. "Pattern Reversal ERG with LED-Stimulation Using Cyclic Summation Technique", Documenta Ophthalmologica 2006, vol. 112, p. 53-60, January.

\* cited by examiner

STIMULUS METHOD FOR MULTIFOCAL VISUAL EVOKED POTENTIAL

FIELD OF THE INVENTION

The present invention relates generally to a method and apparatus for assessing the integrity of the visual field by objective electrophysiological recording using different stimulus sequences for parts of the visual field. In particular, it relates to a method and apparatus for providing an improved stimulus for use in diagnosing and assessing the extent of visual field loss.

BACKGROUND

The objective assessment of the visual field using multifocal stimulation has been described recently in a number of publications, including: "*The topography of visual evoked response properties across the visual field*", Baseler H A et al., Electroencephal. Clin. Neurophysiol. 1994; 90: 65-81; "*Multifocal topographic visual evoked potential: improving objective detection of local visual field defects*", Klistorner A I et al., Invest Ophthalmol Vis Sci 1998; 39: 937-950; "*Objective VEP perimetry in glaucoma—Asymmetry analysis to identify early deficits*", Graham S L et al., J Glaucoma 2000; 9: 10-19; "*Objective perimetry in glaucoma*", Klistorner A and Graham S L, Ophthalmology 2000; 107: 2283-2299; "*Multifocal VEP and ganglion cell damage: applications and limitations for the study of glaucoma*", Hood D C et al., Progress in Retinal & Eye Research 2001; 22: 201-251; "*A Multifocal objective perimetry in the detection of glaucomatous field loss*", Goldberg I. et al., American Journal of Ophtalmology 2002; 133: 29-39; "*Clinical application of the multifocal VEP in glaucoma practice*", Graham, S L et al., Arch Ophthalmol 2005; 123, 729-793.

Using different types of multifocal stimulus presentation, it is possible to perform simultaneous stimulation of a large number of locations of the visual field. Such multifocal stimulus presentations are described, for example, in U.S. Pat. No. 4,846,567 (Sutter), and International (PCI) Application No. PCT/AU00/01483 (Malov, I.). It is possible to record visually evoked cortical potentials (VEP) and electroretinograms (ERG) from all areas of the visual field. For the VEP, various electrode placements have been used.

One representation of the visual field is reported with multichannel bipolar recordings, as described in "*Objective perimetry in glaucoma*", Klistorner A. et al., Ophthalmology 2000; 107: 2283-2299, and International (PCT) Application No. PCT/AU99/00340 (Klistorner A et al.) and corresponding U.S. Pat. No. 6,477,407. Good correlation has been described between the multifocal VEP and visual held loss in glaucoma, and with the delay of multifocal VEP latency in optic neuritis in "*Multifocal Visual Evoked Potential analysis of inflammatory or demyelinating optic neuritis*", Fraser, C et al., Ophthalmology 2006, 113, 315-323.

The stimulus has traditionally been presented on a cathode ray tube (CRT) screen with high luminance and contrast characteristics to a subject undergoing examination. The use of virtual reality goggles has also been described in International (PCT) Application No. PCT/AU01/00423 (Graham S L et al.). However, not all current screens are suitable for standard rapid pseudorandom sequence presentation, due to slow response times and/or decay rates of those screens. In particular, Liquid Crystal Display (LCD) screens and LCD-based goggles exhibit relatively slow decay rates and are consequently less than optimal for displaying stimuli to patients.

Different modes of stimulation have been described. One of the more commonly used modes of stimulation is rapid reversal driven by m-sequences, as described, for example, in "*The topography of visual evoked response properties across the visual field*", Baseler H A et al., Electroencephal. Clin. Neuophysiol. 1994; 90: 65-81, "*Multifocal topographic visual evoked potential: improving objective detection of local visual field defects*", Klistorner A I et al., Invest Ophthalmol Vis Sci 1998; 39: 937-950; "*Objective VEP perimetry in glaucoma—Asymmetry analysis to identify early deficits*", Graham S L et al., J Glaucoma 2000; 9: 10-19, "*Objective perimetry in glaucoma*", Klistorner A et al., Ophthalmology 2000; 107: 2283-2299, "*Multifocal VEP and ganglion cell damage: applications and limitations for the study of glaucoma*", Hood D C et al., Progress in Retinal & Eye Research 2001; 22: 201-251. Alternative modes include use of families of sequences as described by Malov (International (PCT) Application No, PCT/AU00/01483) and used clinically in several studies, such as, for example, "*Multifocal objective perimetry in the detection of glaucomatous field loss*", Goldberg I et al, American Journal of Ophthalmology 2002; 133: 29-39, "*Clinical application of the multifocal VEP in glaucoma practice*", Graham, S L et al., Arch Ophthalmol 2005, 123, 729-793. Other modes of stimulation, such as very slow stimulation rates with pattern pulse stimuli, have also been described, such as, for example, in "*Localization of visually evoked cortical activity in humans*", Srebro, R., J Physiol 1985, 360: 233-246, and "*The topography of scalp potentials evoked by pattern pulse stimuli*", Srebro, R., Vision Research, 1987, 27: 901-914. This was recently revisited as a technique in "*The Pattern-Pulse Multifocal Visual Evoked Potential*", James, A. C., Investigative Opthalmology & Visual Sciences, February 2003, Vol. 44, No. 2.

The derivation of the VEP signal requires multiple repetitions to achieve a good signal to noise ratio (SNR), which in turn determines the total time required to complete a test. The reproducibility of the signal between tests is limited by the SNR of an individual and by differences between test systems.

Thus, a need exists to provide a stimulus protocol that improves VEP signal responses and thus improves SNR with a shortened test time. Further, a need exists to provide a stimulus protocol that is influenced minimally by differences in screen characteristics, such as slow decay rate.

SUMMARY

It is an object of the present invention to overcome substantially, or at least ameliorate, one or more disadvantages of existing arrangements for multifocal VEP recording.

According to a first aspect of the present disclosure, there is provided a method of producing a stimulus for electrophysiological assessment of a visual field, the method comprising the steps of:

generating a pseudorandom sequence of elements selected from at least two different element types, wherein elements of the sequence are assigned equal time intervals; and displaying the pseudorandom sequence, wherein:

each element of a first element type is associated with a baseline value, the baseline value being constant throughout a respective assigned time interval; and each time interval assigned to an element of a second element type is divided into a plurality of portions, each successive portion being associated with a display value of the element, wherein display values associated with adjacent portions differ from one another, and further wherein display values associated with at least two of the portions are different from the baseline value.

According to a second aspect of the present disclosure, there is provided a method of producing a stimulus for electrophysiological assessment of a visual field, the method comprising the steps of:

generating a pseudorandom sequence of elements selected from at least two different element types, wherein elements of the sequence are assigned equal time intervals; and displaying the pseudorandom sequence, wherein:

each element of a first element type is associated with a first display characteristic, the first display characteristic being constant throughout a respective assigned time interval; and each element of a second element type is associated with a second display characteristic for a first portion of the assigned time interval, and a third display characteristic for a second portion of the assigned time interval, wherein each of the first, second and third display characteristics are different from each other.

According to a third aspect of the present disclosure, there is provided a method of producing a stimulus for electrophysiological assessment of a visual field, said method comprising the steps of:

generating a pseudorandom sequence of at least two different element types, wherein elements of said sequence are assigned equal time intervals; and displaying said pseudorandom sequence, wherein:

each element of said first element type is associated with at least one of a constant intensity, constant contrast, and constant colour throughout said time intervals corresponding to said elements of said first element type; and at least one of an intensity, contrast and colour of each element of said second element type is varied in a predetermined manner from an initial value during an initial portion of said tine intervals corresponding to elements of said second element type to a first intermediate value during at least one intermediate portion of said time intervals corresponding to elements of said second element type to a final value during a final portion of said time intervals corresponding to elements of said second element type.

According to a fourth aspect of the present disclosure, there is provided a method of producing a stimulus for electrophysiological assessment of a visual field, said method comprising the steps of:

generating a pseudorandom sequence of at least two different element types, wherein dements of said sequence are assigned equal time intervals;

displaying each element of a first element type, wherein at least one of display intensity, contrast, and colour is constant throughout said assigned time intervals; and displaying each element of a second element type, wherein a predetermined first display characteristic is associated with a first portion of said assigned time intervals, said first display characteristic varying during a second portion of respective assigned intervals.

According to a fifth aspect of the present disclosure, there is provided a system for assessing a visual field of a subject, the system comprising:

at least one recording electrode for obtaining one or more signals from a subject;

a generating means for generating a pseudorandom sequence of elements selected from at least two different element types, wherein elements of the sequence are assigned equal time intervals, each element of a first element type being associated with a baseline value, the baseline value being constant throughout a respective assigned time interval, and each time interval assigned to an element of a second element type being divided into a plurality of portions, each successive portion being associated with a display value of the element, wherein display values associated with adjacent portions differ from one another, and further wherein display values associated with at least two of the portions are different from the baseline value;

a display for displaying the generated pseudorandom sequence; and processing means for processing signals received from the at least one recording electrode in response to the displayed pseudorandom sequence.

According to a sixth aspect of the present disclosure, there is provided a computer program product having a computer readable medium having a computer program recorded therein for generating a stimulus for electrophysiological assessment of a visual field, said computer program product comprising:

computer program code means for generating a pseudorandom sequence of at least two different element types, wherein elements of said sequence are assigned equal time intervals;

computer program code means for displaying each element of a first element type, wherein at least one of display intensity, contrast and colour is constant throughout said assigned time intervals; and computer program code mean for displaying each element of a second element type, wherein a predetermined first display characteristic is associated with a first portion of said assigned time intervals, said first display characteristic varying during a second portion of respective assigned intervals.

According to another aspect of the present disclosure, there is provided an apparatus for implementing any one of the aforementioned methods.

According to another aspect of the present disclosure, there is provided a computer program product including a computer readable medium having recorded thereon a computer program for implementing any one of the methods described above.

Other aspects of the invention are also disclosed.

BRIEF DESCRIPTION OF THE DRAWINGS

One or more embodiments of the present invention will now be described with reference to the drawings, in which.

DETAILED DESCRIPTION

Figure 1:
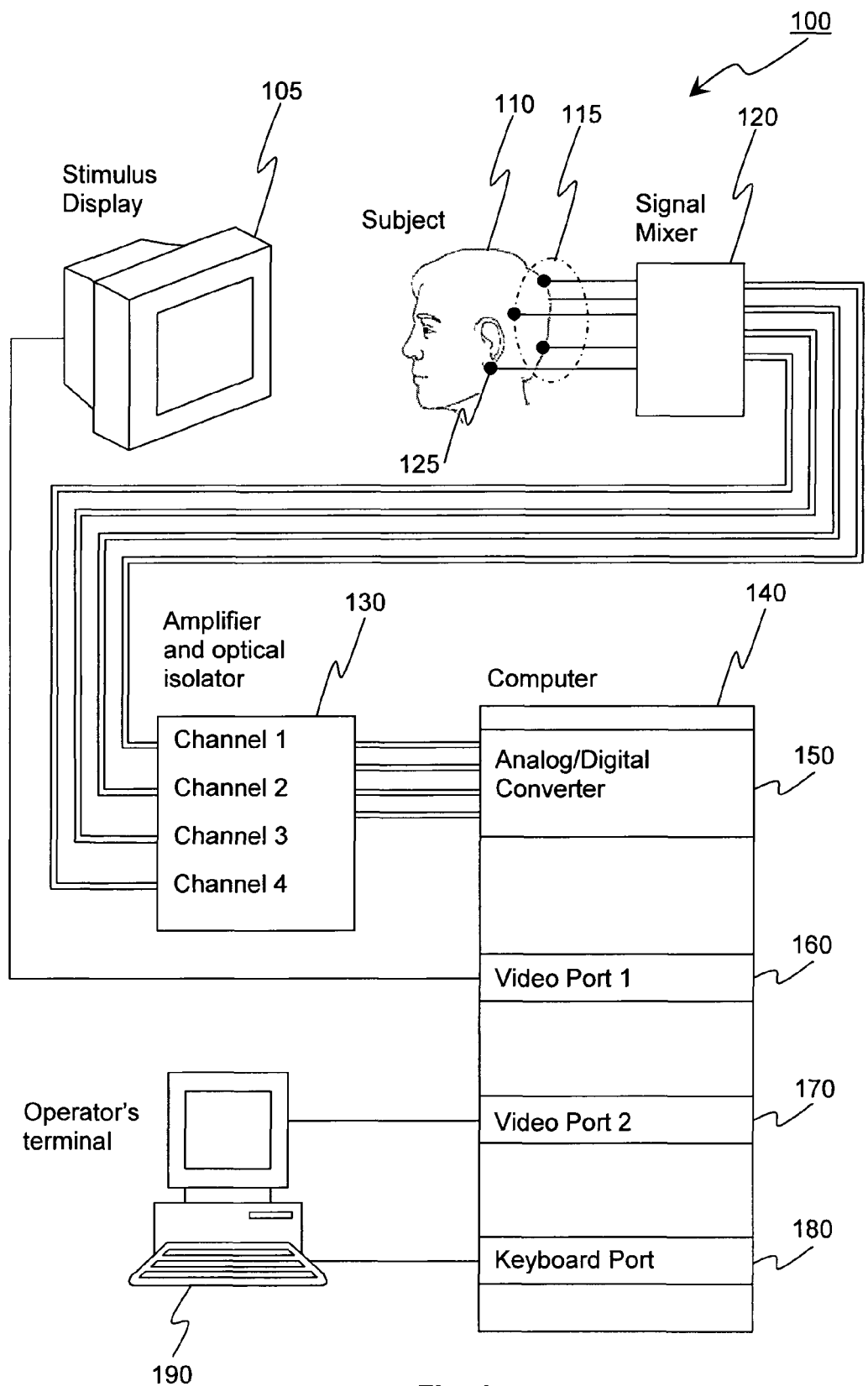
FIG. 1 shows a schematic block diagram representation of a visual field assessment system in accordance with an embodiment of the present disclosure.

Disclosed herein are a method, an apparatus, and a computer program product for providing an improved stimulus for use in objectively assessing the visual field of a subject and recording visual evoked responses. In particular, the present disclosure provides a stimulus that varies in intensity, contrast, or colour, or a combination thereof, over time. In one embodiment, a slow sequence multifocal pattern is provided with "fade to grey" contrast characteristics that enhance VEP signal responses and minimize the effects of screen characteristics. Consequently, low cost LCD screens or LCD-based goggles can be utilised to display the stimulus with excellent and reproducible responses. In another embodiment, a multifocal flash is presented to a subject in order to record a resultant electroretinogram. In this embodiment, the intensity of the multifocal flash is varied over time.

Where reference is made in any one or more of the accompanying drawings to steps and/or features, which have the same reference numerals, those steps and/or features have for the purposes of this description the same function(s) or operation(s), unless the contrary intention appears.

Some portions of the description which follows are explicitly or implicitly presented in terms of algorithms and symbolic representations of operations on data within a computer memory. These algorithmic descriptions and representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that the above and similar terms are to be associated with the appropriate physical quantities and are merely convenient labels applied to these quantities. Unless specifically stated otherwise, and as apparent from the following, it will be appreciated that throughout the present specification, discussions utilizing terms such as "scanning", "calculating", "determining", "replacing", "generating" "initializing", "outputting", or the like, refer to the action and processes of a computer system, or similar electronic device, that manipulates and transforms data represented as physical (electronic) quantities within the registers and memories of the computer system into other data similarly represented as physical quantities within the computer system memories or registers or other such information storage, transmission or display devices.

The present specification also discloses apparatuses for performing the operations of the methods described herein. Such apparatus may be specially constructed for the required purposes, or may comprise a general purpose computer or other device selectively activated or reconfigured by a computer program stored in the computer. The algorithms and displays presented herein are not inherently related to any particular computer or other apparatus. Various general purpose machines may be used with programs in accordance with the teachings herein. Alternatively, the construction of more specialized apparatus to perform the required method steps may be appropriate. The structure of a conventional general purpose computer will appear from the description below.

In addition, the present invention also implicitly discloses a computer program, in that it would be apparent to the person skilled in the art that the individual steps of the preferred method described herein are to be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention. Furthermore, one or more of the steps of the computer program may be performed in parallel rather than sequentially.

Such a computer program may be stored on any computer readable medium. The computer readable medium may include storage devices such as magnetic or optical disks, memory chips, or other storage devices suitable for interfacing with a general purpose computer. The computer readable medium may also include a hard-wired medium such as exemplified in the Internet system, or wireless medium such as exemplified in the GSM mobile telephone system. The computer program when loaded and executed on such a general-purpose computer effectively results in an apparatus that implements the steps of a corresponding method.

One embodiment in accordance with the present disclosure utilises a multifocal stimulator, such as VERIS, Retiscan, ObjectiVision AccuMap or the like, to generate a stimulus which is projected onto a screen. The screen may include, but is not limited to, one or more of a cathode ray tube (CRT), a liquid crystal display (LCD), a light emitting diode (LED) display, a plasma display, and a headmounted system, such as virtual reality (VR) goggles. Amplification of electrophysiological response signals obtained via appropriate electrodes placed on a patient allows the recording of the electrophysiological response of a patient viewing the screen on which the stimulus is displayed. Cross-correlation techniques, such as those described in International (PCT) Application No. PCT/AU00/01483 (Malov I.), allow for derivation of a signal from pseudorandom stimulation and isolation of the signal from background noise. A topographical map of the responses is then derived corresponding to the field of view of the subject. It is then possible to analyse the results, for example by printing the output and comparing the results a database of normal responses.

As mentioned above, the present disclosure provides a stimulus having a display characteristic that varies over time. The display characteristic may be one of a display contrast, intensity, or colour, or a combination thereof. In one embodiment, the stimulus is driven by a pseudorandom sequence that consists of equal numbers of 2 elements (1 and 0) distributed in a random order. Each element of the sequence can be represented by an equal number of frames of the screen. For element "1", which is "pattern-on", all frames contain the stimulating pattern, but the contrast, intensity, or colour of the pattern, or a combination thereof, varies over time. In one embodiment, the contrast, intensity, or colour of the pattern, or a combination thereof, gradually diminishes with sequential frames so there is no abrupt offset. The rate of reduction in contrast or luminance, or the rate of change of colour, is variable, but the stimulus preferably persists to the last frame of that element. For element 0, there is diffuse illumination of the area throughout. Alternatively, the screen is black for element 0. The level of contrast, intensity or colour, or a combination thereof, at which element 0 is displayed may be considered a baseline value, wherein a display characteristic of each instance of element 1 is greater than the baseline value for at least part of an associated time interval. The duration for each of the two elements is equal. In another embodiment, ternary sequences are utilised.

The stimulus pattern may be displayed to a subject in a monocular or binocular manner.

In one embodiment, the colour of a stimulus varies over a time interval. A dark, solid colour, such as black, is utilised as a baseline value for displaying element 0. When displaying element 1, the colour of the stimulus changes over an associated time interval. In one particular embodiment, the colour of the stimulus changes from blue to yellow. In another embodiment, the saturation or hue of the stimulus changes over the time interval. For example, a dark blue stimulus changes to royal blue and then to sky blue over the time interval. In other embodiments, coloured patterns are utilised, rather than solid colours. In further embodiments, a light colour is utilised as a baseline value. As indicated above, other embodiments vary a combination of two or more of the display contrast, intensity and colour of the stimulus over a time interval.

FIG. 1 is a schematic block diagram representation of a visual field assessment system (100) in accordance with an embodiment of the present disclosure. A computer (140) with a linked video board is utilised to generate a pseudorandom stimulus sequence that is presented via a first video port (160) to a stimulus display (105). The stimulus display (105) may be implemented by using, for example, a CRT screen, an LCD screen, a LED display screen, a plasma screen, or head-mounted goggles. However, it will be appreciated by a person skilled in the art that other displays may equally be utilised without departing from the spirit and scope of the present invention.

In the embodiment of FIG. 1, at least one recording electrode (110) is placed on the scalp of a subject (115), and a ground reference electrode (125) is connected to an ear lobe of the subject (115). The recording electrodes (110) and ground reference electrode (125) detect VEP signals from the subject (110). The VEP signals are presented to a signal mixer (120), which mixes the VEP signals into a desired number of channels. The channels are output from the signal mixer (120) to an amplifier and optical isolator (130). The amplifier (130) amplifies the channel signals and presents the amplified signals to the computer (140) via an Analog/Digital converter (150), for processing and display on an operator terminal (190). Video signals are output from the computer (140) to the operator terminal (190) via a second video port (170). The operator terminal (190) allows an operator to view and analyse responses from the subject (110). The operator terminal presents commands to the computer (140) via a keyboard port (180) on the computer (140). One or both of the computer (140) and the operator terminal (190) can be used to compare responses from the subject (110) to normal reference values associated with the pseudorandom stimulus sequence displayed on the stimulus display (105).

Figure 2:
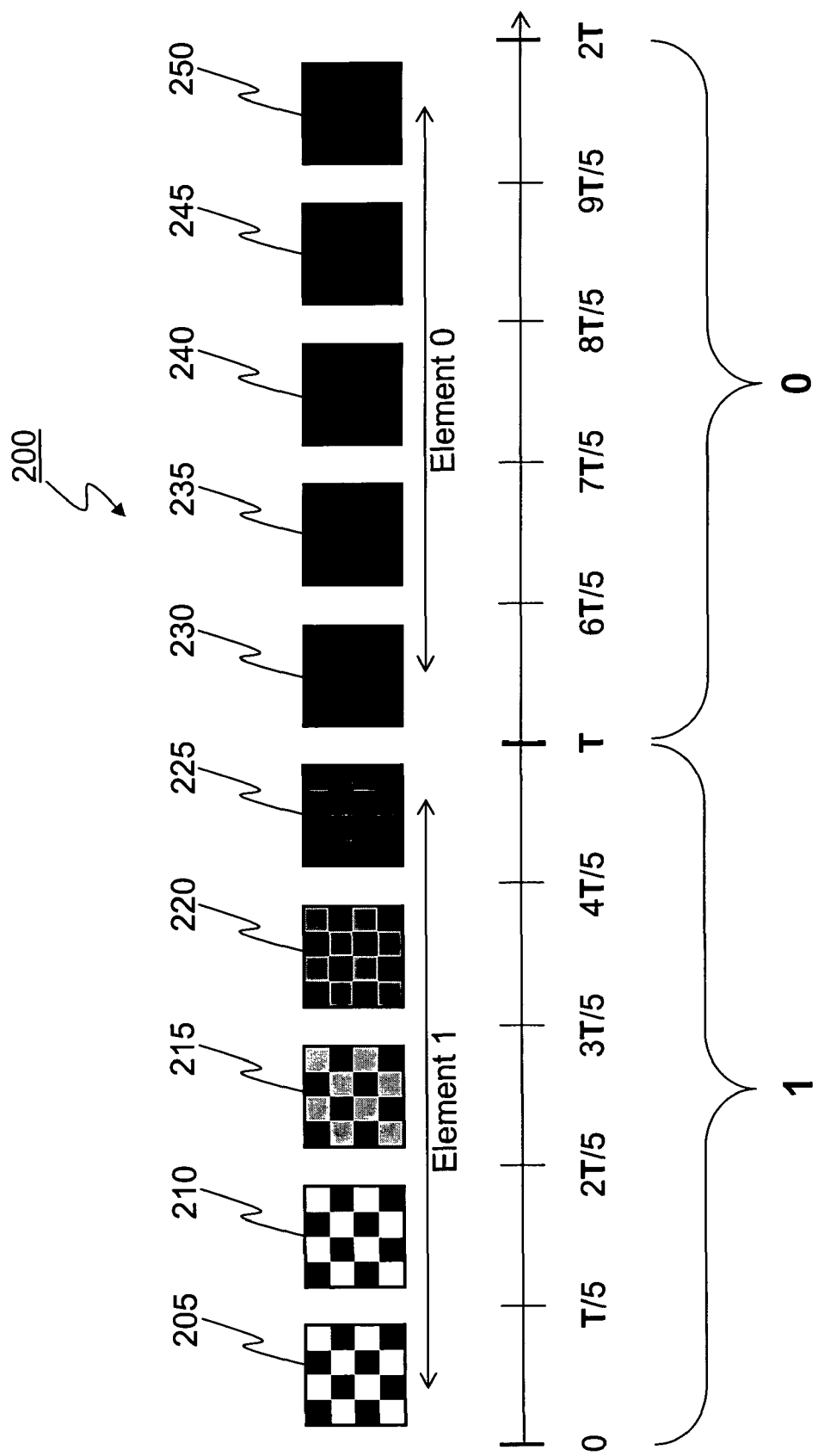
FIG. 2 shows a pseudorandom stimulus sequence presented in accordance with an embodiment of the present disclosure.

FIG. 2 shows an example of a portion of a pseudorandom stimulus sequence (200) over two time intervals (2T). Each element in the pseudorandom stimulus pattern is allocated an equal time interval. In particular, FIG. 2 illustrates the display of element "1", with a gradually fading "pattern on" component, followed by element "0" of neutral background for an equal length of time. The stimulus pattern shown in FIG. 2 is a chequerboard consisting of small, alternating black and white squares. It will be appreciated by a person skilled in the art that other stimulus patterns may equally be utilised without departing from the spirit and scope of the invention. In particular, the stimulus pattern may be an achromatic or chromatic pattern, including but not limited to blue/yellow and red/green patterns.

In accordance with an embodiment of the present disclosure, the intensity, contrast, or colour of the chequerboard pattern, or a combination thereof, is varied over the entire duration of a single time interval (T) when displaying element "1". In the embodiment of FIG. 2, a frame duration of 15 ms is utilised, with each time interval (T) consisting of 5 frames. Thus, each time interval T in this embodiment is 75 ms. At the beginning of the time interval, the chequerboard pattern is displayed at a display value of maximum intensity. Over the course of the time interval, the intensity of the chequerboard decreases. In particular, the embodiment shown in FIG. 2 displays the stimulus pattern at a maximum intensity display value for the initial two frames, during a first portion of the time interval, and then the intensity of the stimulus pattern decreases in the remaining three frames of the time interval (T), during one or more successive portions of the time interval, to subsequent display values, thus producing a stepped-intensity effect for the stimulus pattern. In another embodiment, the colours of the chequerboard pattern are varied. In one embodiment, the colours vary at a constant level of display contrast and intensity. In a further embodiment, the colours of the chequerboard pattern vary and one or both of the display contrast and intensity also vary over the time interval.

Figure 3:
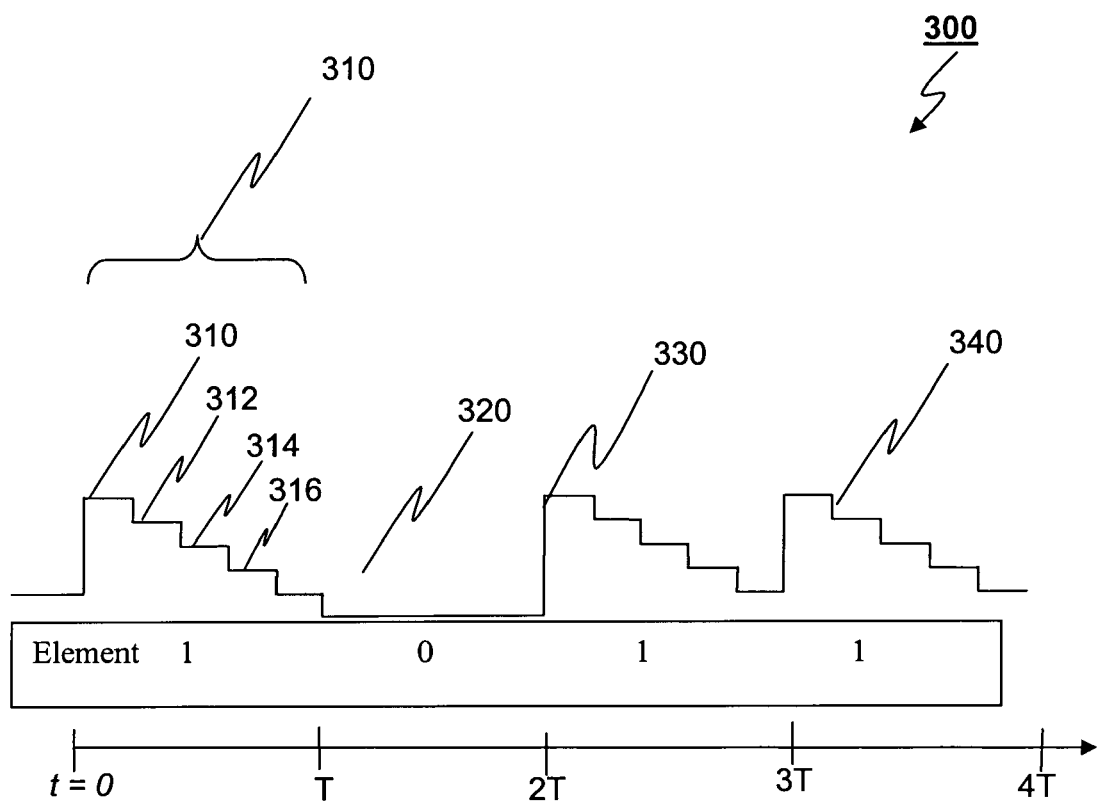
FIG. 3 is a schematic representation of the intensity of the stepped stimulus of FIG. 2 over time.

FIG. 3 is a schematic representation (300) of the intensity of a portion of a pseudorandom sequence, in which the intensity of a stimulus is reduced with each frame. FIG. 3 is described in greater detail below. The stimulus provided by any of these embodiments, and as further described below, is referred to as a saw tooth stimulus profile (STSP), due to the overall shape of the stimulus intensity over time.

Returning to FIG. 2, stimulus pattern (205) shows a chequerboard pattern of maximum intensity at time t=0, corresponding to a first frame a first time interval (T). The maximum intensity of the chequerboard pattern is retained for the second frame, shown as stimulus pattern (210). In the subsequent three frames of the first time interval, the intensity of the chequerboard image decreases in a predetermined manner. Thus, the stimulus pattern (215) of the third frame shows a chequerboard pattern of slightly decreased intensity, relative to stimulus pattern (205) and stimulus pattern (210). The fourth frame shows the chequerboard stimulus pattern (220) at a further decreased intensity. During the fifth and final frame of the first time interval, the intensity of the displayed chequerboard stimulus pattern (225) has diminished significantly from the chequerboard displayed at time t=0, but nevertheless, the chequerboard stimulus pattern is still visible.

The second time interval in the sequence "10" of FIG. 2 is occupied by the "0" signal. In this embodiment, a grey square is displayed for the duration of the second time interval, as seen in each of the frames of the second time interval (230, 235, 240, 245, and 250).

In the embodiment described above with reference to FIG. 2, the intensity of a stimulus pattern corresponding to a "1" is decreased in a predetermined manner to produce a stepped stimulus profile. The predetermined manner associated with the embodiment of FIG. 2 retains maximum intensity of the stimulus pattern for the first two frames of a five frame time interval, with subsequent frames displaying a stimulus pattern of reduced intensity to produce a stepped stimulus pattern.

An alternate embodiment displays the stimulus pattern at a maximum intensity for an initial frame, with subsequent frames displaying the stimulus pattern at half of the intensity of the preceding frame.

Decreasing the intensity of the stimulus in a controlled manner provides a more pleasant viewing experience for a patient, relative to the sharp flicker experienced with other stimulus displays. Further, the controlled reduction in stimulus intensity controls the perceived decay rate of the display screen. Other embodiments vary the contrast of the stimulus, the colour of the stimulus, or a combination of two or more of the intensity, contrast and colour of the stimulus.

FIG. 3 is a schematic representation (300) of the intensity of a portion of a pseudorandom sequence consisting of "1011" and presented to a display using the stepped stimulus in accordance with an embodiment of the present disclosure. In this embodiment, intensity of a stimulus pattern for element "1" is decreased in equal steps across a time interval, while maintaining that the stimulus pattern is still visible in the final frame of a time interval. In the embodiment of FIG. 3, a time interval consists of five frames. Thus, the initial element "1" is presented as five frames, followed by five frames representing the element "0", followed by five frames representing the element "1", and a final five frames representing the element "1".

At a time t=0, an initial frame of element "1" displays a stimulus pattern (310) with maximum intensity. A second frame displays the stimulus pattern (312) of reduced intensity. As indicated above, the embodiment of FIG. 3 utilises time intervals of five frames and the stimulus pattern for an element "1" is reduced in equal steps across the time interval. Accordingly, the intensity of the stimulus pattern (312) is ⅘ the intensity of stimulus pattern (310) from the first frame. A third frame shows a stimulus pattern (314) that is ⅗ the intensity of the stimulus pattern (310). Fourth and final frames of the first time interval show a stimulus pattern (316) that is ⅖ and ⅕, respectively, of the intensity of the initial stimulus pattern (310). The first time interval t=0 to t=T produces a first stepped stimulus pattern (305).

From time t=T to t=2 T, the element "0" is displayed. The element "0" is preferably displayed using a grey square for each frame within the relevant time interval. From time t=2 T to t=3 T, the element "1" is represented in a manner similar to that described above with respect to the first time interval, producing a second stepped stimulus pattern (330). Similarly, the third element "1" in the sequence "1011" produces a third stepped stimulus pattern (340).

It will be appreciated by a person skilled in the art that other time intervals and frame rates may equally be used without departing from the spirit and scope of the invention.

The example described above with respect to FIG. 3 relates to a stimulus in which the intensity decreases over time. In an alternate embodiment, the intensity, contrast, or colour of a stimulus corresponding to element 1 is increased over time, producing a rising stepped profile. Alternatively, a combination of two or more of the intensity, contrast, and colour of the stimulus is increased over time. In a further embodiment, the intensity, contrast, or colour of a stimulus, or a combination thereof, is increased to a maximum value and then decreased within the frame duration of element 1. In a yet further embodiment, the intensity, contrast, or colour of a stimulus, or a combination thereof, is decreased to a minimum value and then increased within the frame duration of element 1. It will be appreciated by a person skilled in the art that other variations of the intensity, contrast, or colour of a stimulus may equally be practised without departing from the spirit and scope of the invention.

The stimulation technique disclosed herein produces a sharp pattern onset stimulus with an appropriate recovery time for cortical gain mechanisms, such that signal amplitude is enhanced, as previously described in conventional VEP recording. See, for example, "*Localization of visually evoked cortical activity in humans*", Srebro, R., J Physiol 1985:360, 233-246, "*The topography of scalp potentials evoked by pattern pulse stimuli*", Srebro, R, Vision Research, 1987, 27: 901-914, and "*Source localization of pattern specific components of human visual evoked potentials: II Component of extra-striate cortical origin*", Jeffries, D A et al., Exp Brain Research, 1972, 16, 22-40. However, the offset of the pattern is gradual, rather than a pattern pulse. The overall descriptive term for this type of stimulus has been termed "saw tooth stimulus profile" (STSP) due to the shape of the onset/offset intensity over time. One advantage of this method is that any type of screen cart be used, regardless of the screen response/decay time. Additionally, the STSP stimulus is easier far the subject to view than pattern pulse or rapid flicker.

Figure 4:
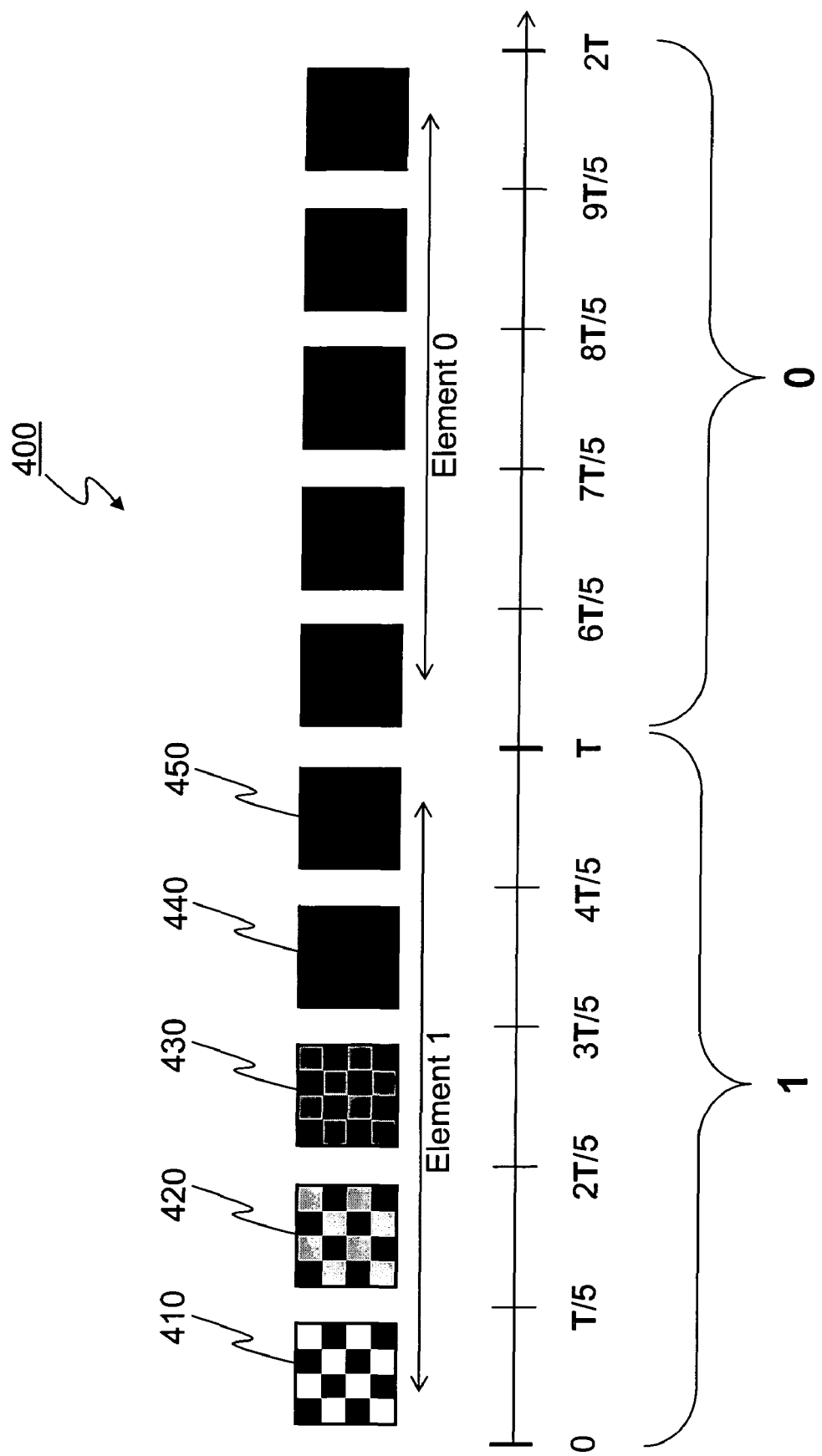
FIG. 4 shows a pseudorandom stimulus sequence presented in accordance with an alternate embodiment of the present disclosure.
Figure 5:
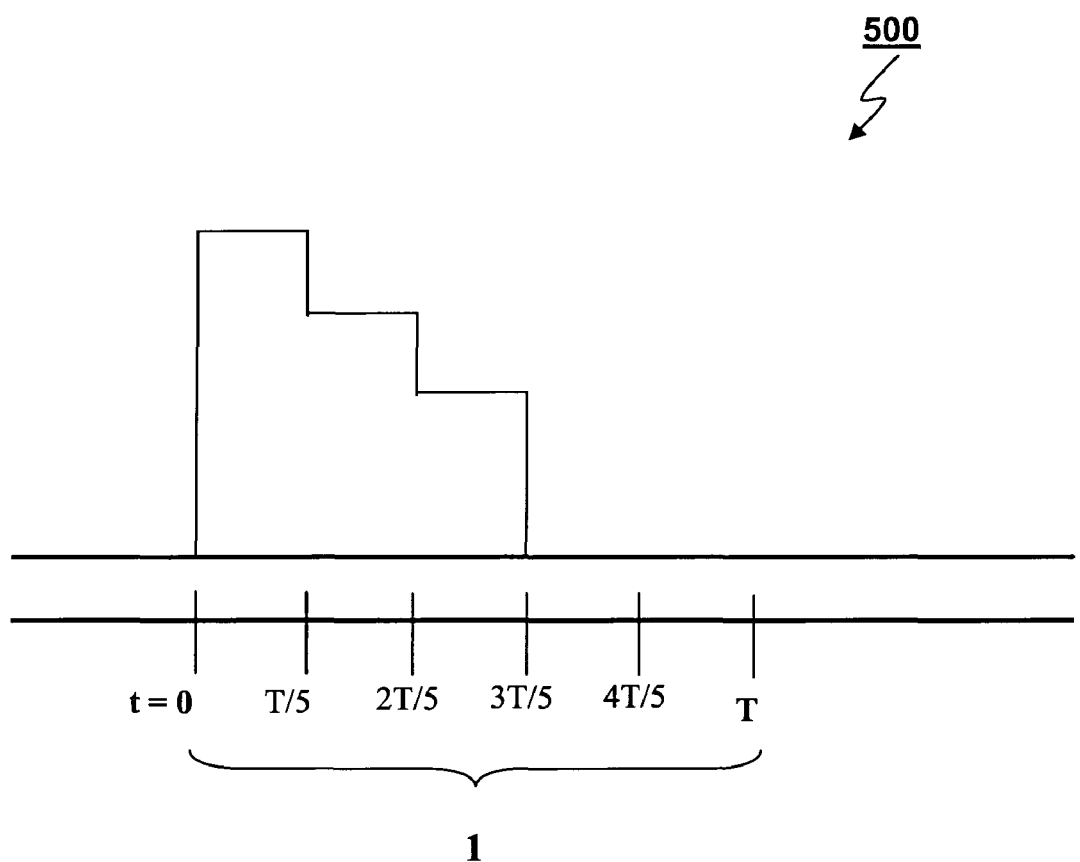
FIG. 5 is a schematic representation of intensity of the stepped pulse stimulus of FIG. 4.

In the embodiments described above, the stimulus pattern for element "1" has presented a pattern for the entire duration of the nominated time interval. That is, each frame it the time interval displays a stimulus pattern. However, an alternate embodiment presents a pulsed stimulus for a portion of the time interval. FIG. 4 shows a schematic representation of intensity of a stepped stimulus pattern in accordance with a further embodiment of the present disclosure. The embodiment of FIG. 4 utilises a time interval consisting of five frames, as described above with reference to FIG. 2. However, in the embodiment of FIG. 4 an element "1" is presented at maximum intensity for an initial frame (410), followed by two frames (420, 430) of decreasing intensity. The remaining two frames of the time interval present grey squares (440, 450). This alternate embodiment produces a stepped pulse stimulus pattern (500), as shown in FIG. 5.

Figure 6:
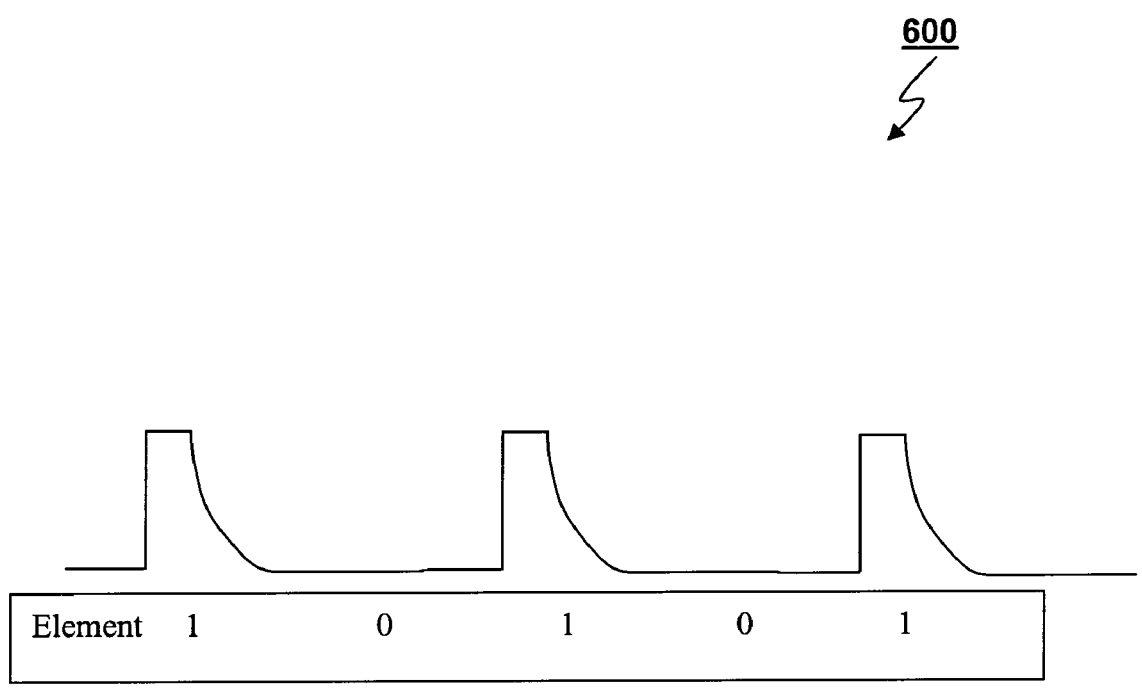
FIG. 6 is a schematic representation of intensity of a stimulus presented in accordance with an alternate embodiment of the present disclosure.

FIG. 6 is a schematic representation of an intensity pattern (600) of a stimulus presented in accordance with an alternate embodiment of the present disclosure. In this embodiment, a stimulus pattern is presented at a maximum intensity for one or more frames. The intensity of the stimulus pattern is then reduced in accordance with a logarithmic decay pattern over the remaining frames of the time interval. The intensity pattern (600) shows a sequence "10101". It is possible for the reduction of the stimulus pattern intensity to occur over the entire duration of a time interval for element "1". Alternatively, the intensity may be decreased over a portion of the time interval, such that one or more final frames of the element "1" are presented as grey squares, or their equivalent.

Figure 7:
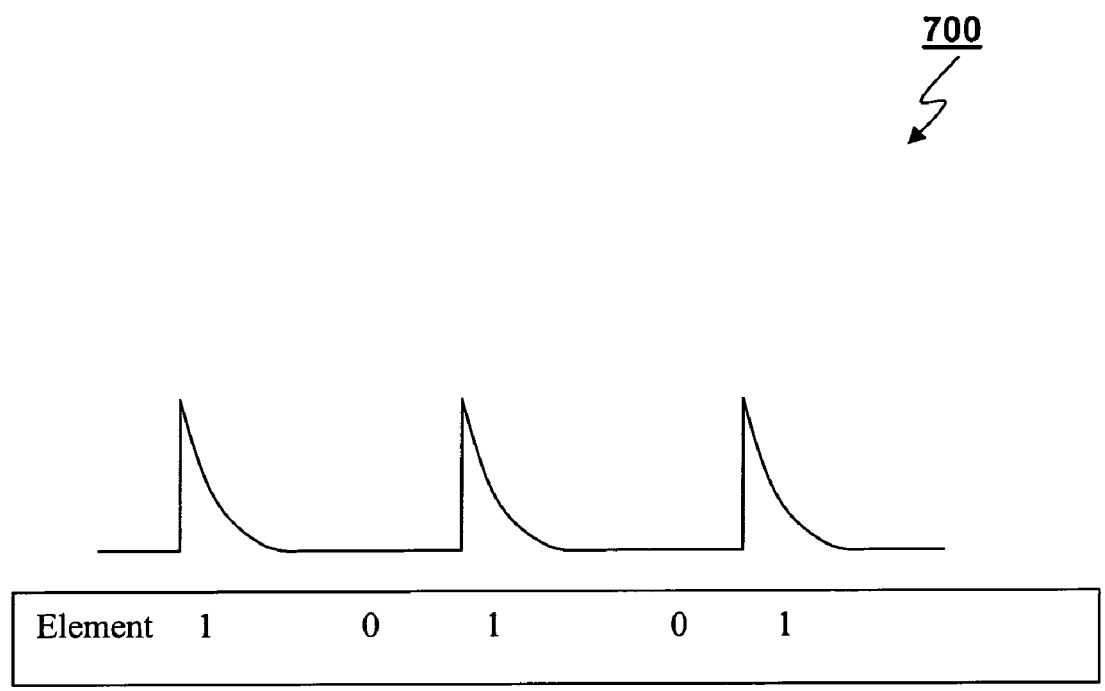
FIG. 7 is a schematic representation of intensity of a stimulus presented in accordance with an alternate embodiment of the present disclosure.

FIG. 7 is a schematic representation of an intensity pattern (700) of a stimulus presented in accordance with an alternate embodiment of the present disclosure. In this embodiment, a stimulus pattern is initially presented at a maximum intensity at the beginning of a first frame. The intensity of the stimulus pattern is then reduced in accordance with a logarithmic decay pattern over the remaining frames of the time interval. The intensity pattern (700) shows a sequence "10101". It is possible for the reduction of the stimulus pattern intensity to occur over the entire duration of a time interval for element "1". Alternatively, the intensity may be decreased over a portion of the time interval, such that one or more final frames of the element "1" are presented as grey squares, or their equivalent.

Figure 8:
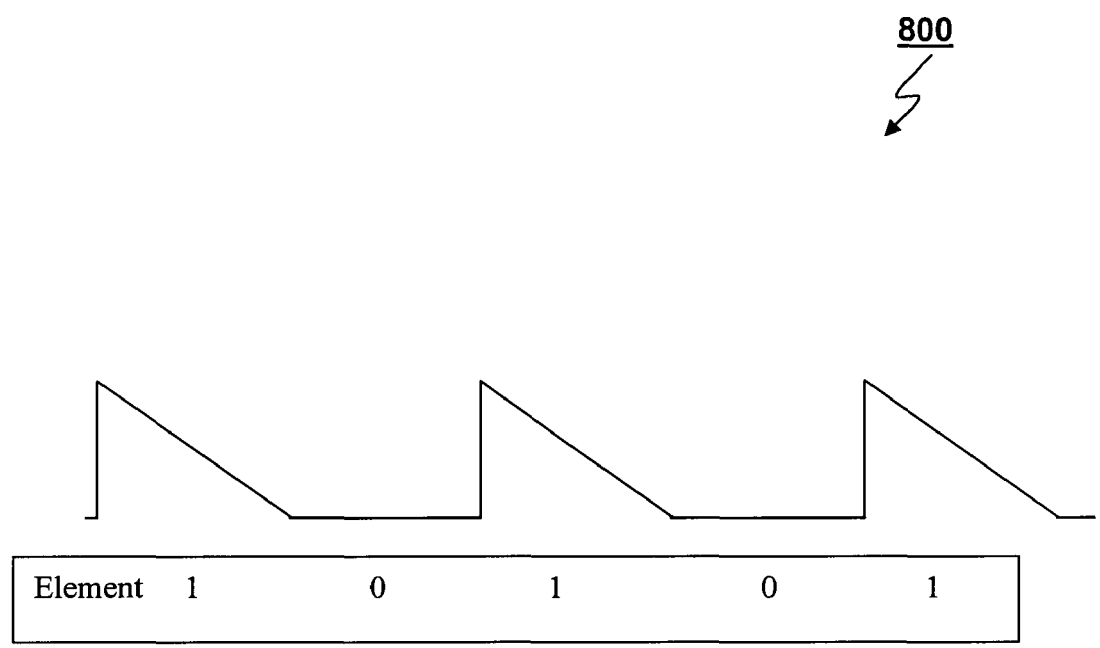
FIG. 8 is a schematic representation of intensity of a stimulus presented in accordance with an alternate embodiment of the present disclosure, in which the stimulus is a pulse stimulus.

FIG. 8 is a schematic representation of an intensity pattern (800) of a stimulus presented in accordance with an alternate embodiment of the present disclosure. In this embodiment, a stimulus pattern is presented at a maximum intensity for a first frame. The intensity of the stimulus pattern is then reduced in accordance with a linear decay pattern over the remaining frames of the time interval. The intensity pattern (800) shows a sequence "10101". It is possible for the reduction of the stimulus pattern intensity to occur over the entire duration of a time interval for element "1". Alternatively, the intensity may be decreased over a portion of the time interval, such that one or more final frames of the element "1" are presented as grey squares, or their equivalent.

The intensity of the stimulus pulse can be varied in a decreasing manner to achieve many other stimulus profiles, without departing from the spirit and scope of the invention. For example, the intensity of the stimulus can decay from a predetermined maximum intensity to a predetermined minimum intensity in accordance with a continuous logarithmic scale. Alternatively, the intensity of the stimulus pulse can equally decay in a linear fashion, as shown in FIG. 8. In a further alternative, the contrast and/or intensity and/or colour of a stimulus pulse is varied in steps of unequal duration.

Figure 9:
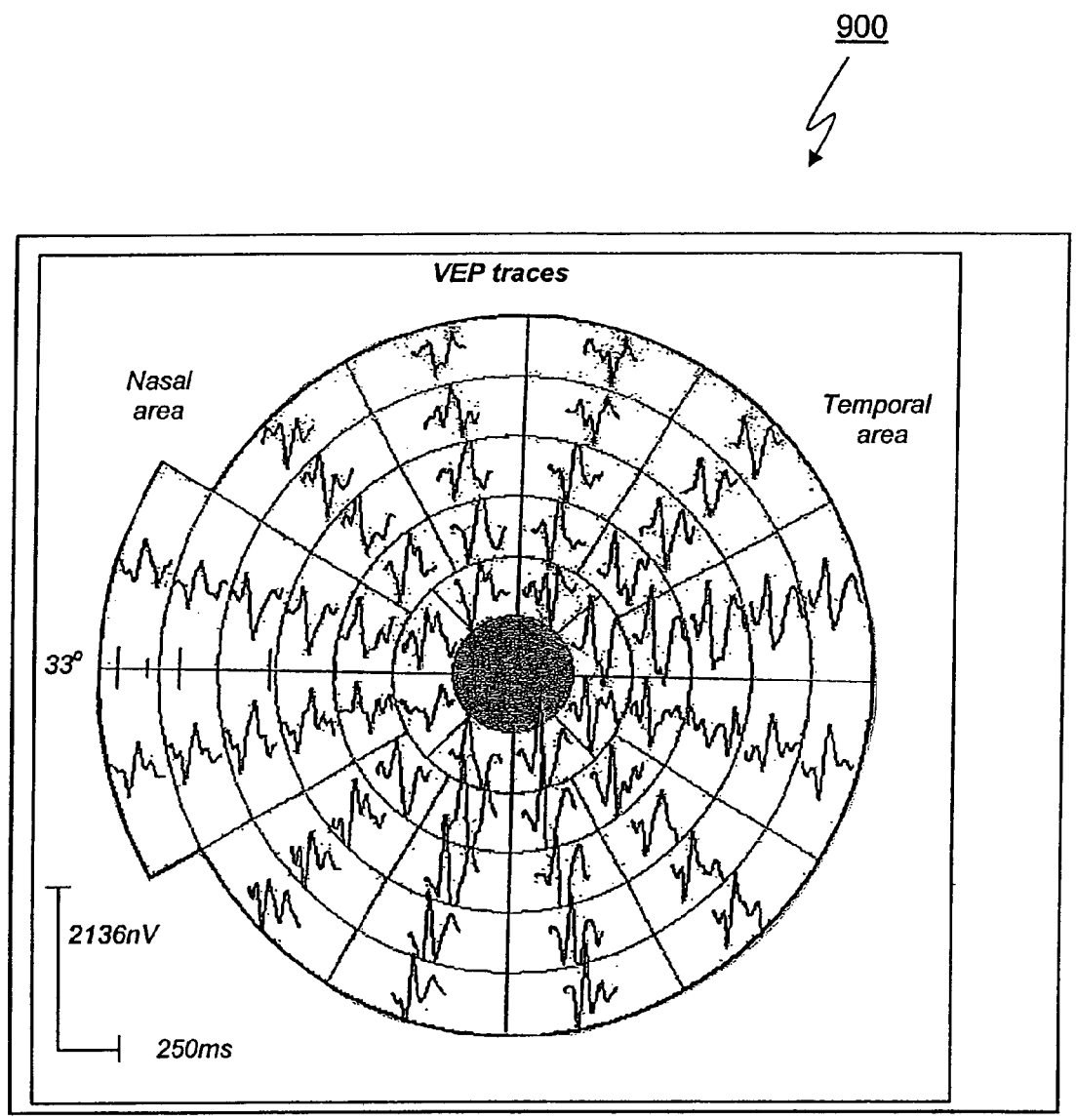
FIG. 9 is a VEP trace.

FIG. 9 is a VEP trace illustrating responses to a stimulus presented in accordance with an embodiment of the present disclosure. FIG. 9 shows a recorded trace array (900) of the multifocal VEP using a stepped multifocal stimulus technique. The recorded trace array (900) shows VEP signals recorded in response to a stimulus presented at fifty-eight test zones within the visual field. The fifty-eight test zones are arranged in a cortically-scaled dartboard configuration in concentric rings, with an innermost ring consisting of eight test zones. Four outer rings consist of twelve test zones each. Two further test zones appear in an arc of an outermost ring. The stimulus was a chequerboard pattern with individual zones presenting according to a pseudorandom sequence.

The right eye of a normal subject was stimulated using a stimulus presented on an LCD screen, and the resulting signals were detected by four recording electrodes placed on the occipital scalp of the subject. The four electrodes were linked in various paired combinations to provide four recording channels, with a reference electrode placed on the ear of the subject. To minimise random noise, multiple presentations were made and the signals averaged, with appropriate amplification and filtering. The individual signals from each of the test zones were derived by cross correlations with the presenting sequence.

For each test location, the largest signal from each of the four channels was selected and shown in the trace array. The detected signals shown in the trace array (900) vary in shape and timing, depending on the local anatomy of that part of the visual cortex from which the signals are derived. Radial sectors tend to have similarly shaped waveforms. For presentation purposes in order to show all the signals, the zones are all drawn as similar size. In the test stimulus, however, the central test zones are usually smaller, and the more peripheral test zones are larger, to take into account the dominance of the central visual field representation in the cortex (cortical scaling of the stimulus).

For a multifocal ERG, single channel recording is sufficient and the waveforms are all of similar shape. The number and distribution of test zones can be varied for the multifocal ERG, with less scaling of stimulus test zone size between central and peripheral fields. The stimulus is usually a local flash, rather than a pattern for each zone. However, it is equally possible to record responses to patterns.

One embodiment in accordance with the present disclosure utilises short periods of stimulation, which produce larger responses from a subject. The testing time required to obtain the required data from the subject has been reduced to approximately five minutes, compared with pre-existing methods in which recording times of seven to twelve minutes are required to elicit the same responses from a subject.

Controlling the display intensity of a stimulus over a predetermined time allows stimulus sequences to be presented on many different display screens. CRTs typically exhibit decay rates in the order of approximately 2 milliseconds, however LCD screens exhibit decay rates in the range of approximately 15 to 25 milliseconds. The actual decay rates can vary considerably between screens of different manufacturers and between screens of different technological generations. Further, expensive LCD screens utilising the latest technology typically exhibit shorter decay rates than cheaper LCD screens utilising older technology.

In the embodiment described above with respect to FIG. 2, a frame duration of 15 ms was utilised. A time interval of 75 ms, corresponding to five frames, was allocated to each element of the stimulus sequence. Using existing methods, an element of a stimulus sequence presented on a CRT screen disappears quickly at the end of an assigned time interval, as the decay rate of CRT screens is relatively short. However, the same element presented on an LCD screen disappears slowly, due to the longer decay rate of the LCD screen. As indicated above, the decay rate of an LCD screen is typically ten times slower than a CRT screen. Consequently, it is difficult to achieve consistent readings from subjects when utilising existing methods on screens with different decay rates.

When a sequence consisting of element "1" followed by element "0" is presented on an LCD screen with a slow decay rate, some of the element "1" pattern is still discernible by a subject during the time interval assigned to the element "0", as the pattern decays. However, the same sequence presented on a CRT screen does not exhibit the same extent of decay of the element "1" pattern during the time interval assigned to element "0". Consequently, it is likely that the electrophysiological responses detected from a subject will differ depending on the type of screen utilised to display the stimulus sequence. Controlling the display intensity of an element of a stimulus sequence in accordance with the present disclosure substantially overcomes the differences in decay rates among different display screens. The display intensity of an element is reduced in a controlled manner over an assigned time interval. At the end of the assigned time interval, the display intensity for the element has been reduced. Consequently, any residual pattern discernible during a subsequent time interval arising from a screen decay rate is reduced. In an embodiment such as that described above with reference to FIG. 2, the display intensity is significantly reduced during the time interval. The intensity of the displayed chequerboard stimulus pattern (225) has diminished significantly from the chequerboard (205) displayed at time t=0. Thus, there will be minimal residual pattern discernible by a subject during a subsequent time interval, even when viewed on a screen with a slow decay rate. Thus, electrophysiological responses are less dependent on the type of display screen utilised, allowing cheaper LCD screens to be used.

The aforementioned preferred method(s) comprise a particular control flow. There are many other variants of the preferred method(s) which use different control flows without departing the spirit or scope of the invention. Furthermore one or more of the steps of the preferred method(s) may be performed in parallel rather sequential.

Figure 10:
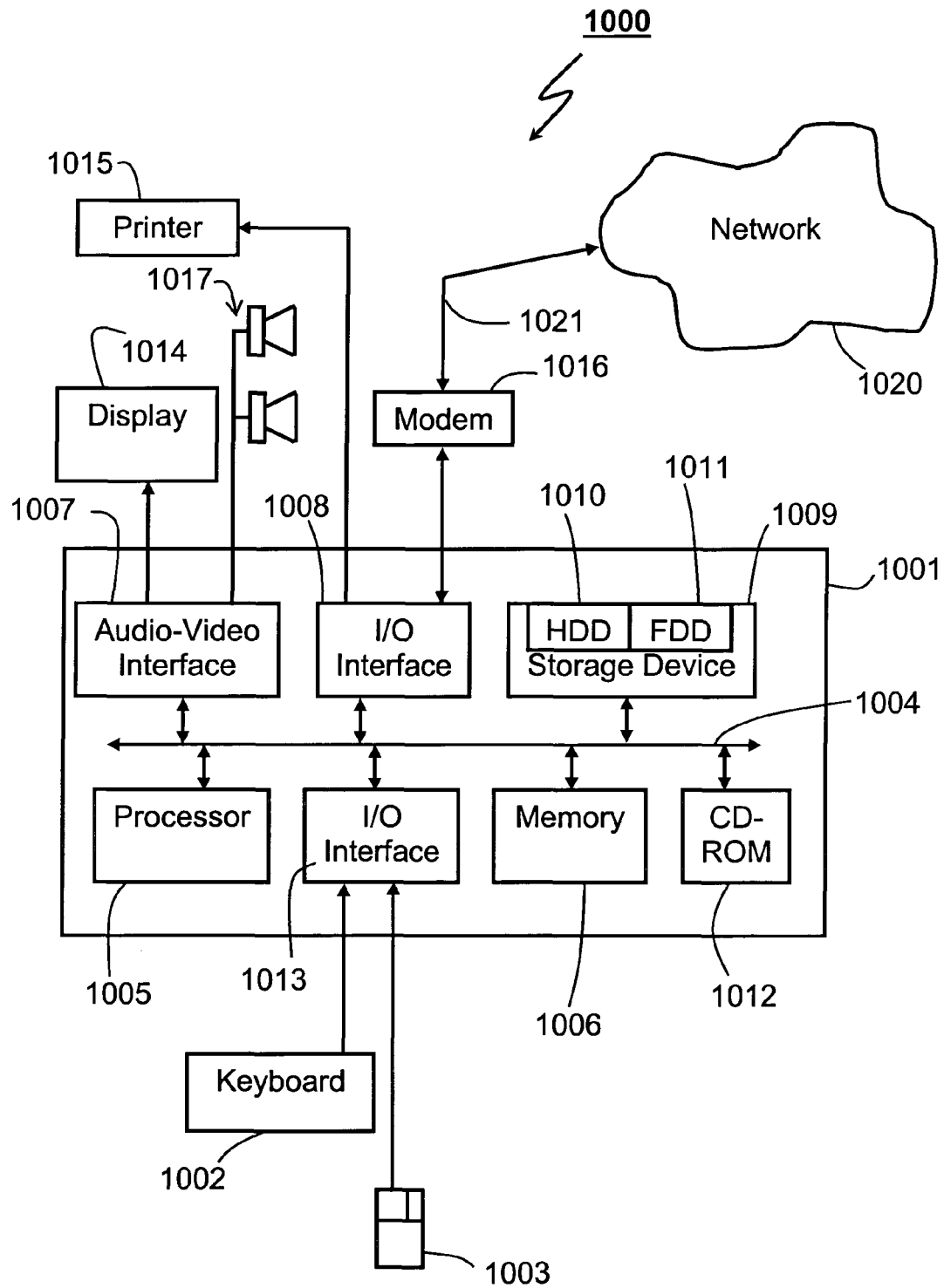
FIG. 10 is a schematic block diagram of a general purpose computer upon which arrangements described herein can be practiced.

The method of providing an improved stimulus is preferably practiced using a general-purpose computer system 1000, such as that shown in FIG. 10 wherein the processes or waveforms of FIGS. 1 to 9 may be implemented as software, such as an application program executing within the computer system 1000. In particular, the steps of the method of providing an improved stimulus are effected by instructions in the software that are carried out by the computer. The instructions may be formed as one or more code modules, each for performing one or more particular tasks. The software may also be divided into two separate parts, in which a first part performs the stimulus generation methods and a second part manages a user interface between the first part and the user. The software may be stored in a computer readable medium, including the storage devices described below, for example. The software is loaded into the computer from the computer readable medium, and then executed by the computer. A computer readable medium having such software or computer program recorded on it is a computer program product. The use of the computer program product in the computer preferably effects an advantageous apparatus for presenting an improved stimulus, particularly for assessing the visual field of a patient.

The computer system 1000 is formed by a computer module 1001, input devices such as a keyboard 1002 and mouse 1003, output devices including a printer 1015, a display device 1014 and loudspeakers 1017. A Modulator-Demodulator (Modem) transceiver device 1016 is used by the computer module 1001 for communicating to and from a communications network 1020, for example connectable via a telephone line 1021 or other functional medium. The modem 1016 can be used to obtain access to the Internet, and other network systems, such as a Local Area Network (LAN) or a Wide Area Network (WAN), and may be incorporated into the computer module 1001 in some implementations.

The computer module 1001 typically includes at least one processor unit 1005, and a memory unit 1006, for example formed from semiconductor random access memory (RAM) and read only memory (ROM). The module 1001 also includes a number of input/output (I/O) interfaces including an audio-video interface 1007 that couples to the video display 1014 and loudspeakers 1017, an I/0 interface 1013 for the keyboard 1002 and mouse 1003 and optionally a joystick (not illustrated), and an interface 1008 for the modem 1016 and printer 1015. In some implementations, the modem 1016 may be incorporated within the computer module 1001, for example within the interface 1008. A storage device 1009 is provided and typically includes a hard disk drive 1010 and a floppy disk drive 1011. A magnetic tape drive (not illustrated) may also be used. A CD-ROM drive 1012 is typically provided as a non-volatile source of data. The components 1005 to 1013 of the computer module 1001, typically communicate via an interconnected bus 1004 and in a manner which results in a conventional mode of operation of the computer system 1000 known to those in the relevant art. Examples of computers on which the described arrangements can be practised include IBM-PC's and compatibles, Sun Sparcstations or similar computer systems.

Typically, the application program is resident on the hard disk drive 1010 and is read and controlled in its execution by the processor 1005. Intermediate storage of the program and any data fetched from the network 1020 may be accomplished using the semiconductor memory 1006, possibly in concert with the hard disk drive 1010. In some instances, the application program may be supplied to the user encoded on a CD-ROM or floppy disk and read via the corresponding drive 1012 or 1011, or alternatively may be read by the user from the network 1020 via the modem device 1016. Still further, the software can also be loaded into the computer system 1000 from other computer readable media. The term "computer readable medium" as used herein refers to any storage or transmission medium that participates in providing instructions and/or data to the computer system 1000 for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external of the computer module 1001. Examples of transmission media include radio or infra-red transmission channels as well as a network connection to another computer or networked device, and the Internet or Intranets including e-mail transmissions and information recorded on Websites and the like.

The method of providing an improved stimulus may alternatively be implemented in dedicated hardware such as one or more integrated circuits performing the functions or sub functions of generating a pseudorandom sequence and presenting an improved stimulus that decreases in intensity over time. Such dedicated hardware may include graphics processors, digital signal processors, or one or more microprocessors and associated memories.

INDUSTRIAL APPLICABILITY

It is apparent from the above that the arrangements described are applicable to the computer, data processing, and healthcare industries.

The foregoing describes only some embodiments of the present invention, and modifications and/or changes can be made thereto without departing from the scope and spirit of the invention, the embodiments being illustrative and not restrictive.

In the context of this specification, the word "comprising" means "including principally but not necessarily solely" or "having" or "including", and not "consisting only of". Variations of the word "comprising", such as "comprise" and "comprises" have correspondingly varied meanings.

The claims defining the invention are as follows:

1. A method of producing a stimulus for electrophysiological assessment of a visual field, said method comprising the steps of
    generating a pseudorandom sequence of elements selected from at least two different element types, wherein elements of said sequence are assigned equal time intervals; and
    displaying said pseudorandom sequence, wherein:
    each element of a first element type is associated with a baseline value, said baseline value being constant throughout a respective assigned time interval; and
    each time interval assigned to an element of a second element type is divided into a plurality of portions, each successive portion being associated with a display value of said element, wherein display values associated with adjacent portions differ from one another, and further wherein display values associated with at least two of said portions are different from said baseline value.

2. The method, according to claim 1, wherein said each successive display value decreases in a predetermined manner.

3. The method according to claim 2, wherein said successive decreasing display values produce a stepped display profile for each element of said second element type.

4. The method according to claim 2, wherein a subset of said successive decreasing display values approximate a continuous curve.

5. The method according to claim 2, wherein all of said display values are different from said baseline value.

6. The method according to claim 1, wherein said baseline value and said display values are levels of display contrast.

7. The method according to claim 1, wherein said baseline value and said display values are levels of display intensity.

8. The method according to claim 1, wherein said each successive display value increases in a predetermined manner.

9. The method according to claim 8, wherein said successive increasing display values produce a stepped display profile for elements of said second element type.

10. The method according to claim 1, wherein said plurality of portions are equal in duration.

11. The method according to claim 1, wherein said baseline value is substantially equal to zero.

12. The method according to claim 1, comprising the further step of: recording at least one electrophysiological response in response to said stimulus.

13. The method according to claim 12, comprising the further steps of: processing said responses; and mapping said processed responses to locations within a visual field.

14. The method according to claim 1, wherein said pseudorandom sequence is displayed on a screen selected from the group of screens consisting of: cathode ray tube screen, liquid crystal display screen, plasma screen, virtual reality goggles, headmounted display, and a light emitting diode display.

15. The method according to claim 1, wherein, said pseudorandom sequence is displayed monocularly.

16. The method according to claim 1, wherein said pseudorandom sequence is displayed binocularly.

17. The method according to claim 1, wherein said stimulus is an achromatic pattern.

18. The method according to claim 1, wherein said stimulus is a chromatic pattern.

19. The method according to claim 1, wherein said pseudorandom sequence is selected from the group of sequences consisting of binary and ternary sequences, and combinations thereof.

20. The method according to claim 1, wherein said baseline value and said display values are colours.

21. A method of producing a stimulus for electrophysiological assessment of a visual field, said method comprising the steps of generating a pseudorandom sequence of elements selected from at least two different element types, wherein elements of said sequence are assigned equal time intervals; and displaying said pseudorandom sequence, wherein:

each element of a first element type is associated with a baseline value, said baseline value being constant throughout a respective assigned time interval; and each time interval assigned to an element of a second element type is divided into a plurality of portions, each successive portion being associated with a display value of said element, wherein the display value of an element of the second element type is reduced in a controlled manner over successive portions of the assigned time interval such that differences in decay rates among different display screens are overcome.

* * * * *